United States Patent
Reinhardt et al.

(10) Patent No.: US 6,217,998 B1
(45) Date of Patent: Apr. 17, 2001

(54) METHOD OF APPLYING MAKEUP AND ARTICLE

(76) Inventors: John G Reinhardt, 1652 Kingsport Dr., Riverside, CA (US) 92506; Craig W Henderson, 7705 Whitewood Dr., Fontana, CA (US) 92336

( * ) Notice: Subject to any disclaimer, the term of this patent is extended or adjusted under 35 U.S.C. 154(b) by 0 days.

(21) Appl. No.: 08/929,824

(22) Filed: Sep. 15, 1997

(51) Int. Cl.[7] ........................................ B32B 5/14
(52) U.S. Cl. .................. 428/308.8; 424/5.64; 424/70.12; 424/78.03; 424/401; 424/402; 427/244; 427/288; 427/336; 427/398.3; 427/429; 427/439; 428/306.6; 428/409; 428/469; 428/522; 428/689; 428/702; 514/946; 514/947
(58) Field of Search ................................ 424/5, 64, 70.12, 424/78.03, 401, 402; 514/946, 947; 427/244, 288, 336, 398.3, 429, 439; 428/306.6, 308.8, 409, 469, 522, 689, 702

(56) References Cited

U.S. PATENT DOCUMENTS

| | | | |
|---|---|---|---|
| 4,559,157 | * | 12/1985 | Smith et al. ........................ 424/401 |
| 4,792,444 | * | 12/1988 | Fukasawa et al. ................... 424/63 |
| 5,382,433 | * | 1/1995 | Pahlck et al. ....................... 424/401 |
| 5,474,805 | * | 12/1995 | Vaughn . |
| 5,496,544 | * | 3/1996 | Mellul et al. ...................... 424/78.03 |
| 5,525,344 | * | 6/1996 | Wivell ................................. 424/401 |
| 5,560,917 | * | 10/1996 | Cohen et al. ........................ 424/401 |
| 5,578,353 | * | 11/1996 | Drew . |
| 5,648,066 | * | 7/1997 | Stepniewski ......................... 424/64 |
| 5,709,848 | * | 1/1998 | Galey et al. .......................... 424/59 |
| 5,931,168 | * | 4/1998 | Abercrombie et al. . |

\* cited by examiner

*Primary Examiner*—Bernard Pianalto
(74) *Attorney, Agent, or Firm*—Woodling, Krost & Rust

(57) ABSTRACT

A method of applying makeup to one's person including the steps of preparing a liquid makeup composition by mixing together a volatile solvent (20–98%), soluble polymer (0.1–20%) and colorant powder (0.1–40%). The solvents, polymers and colorant powders usable in the invention are disclosed herein. The makeup composition is absorbed on an absorbent material which can be natural sponge, synthetic sponge and fiber and the composition on the absorbent material is dried to remove the volatile solvent. Thereafter the absorbent material with dried composition thereon is subjected to a volatile solvent to wet the same and the absorbent material with the composition thereon is rubbed on one's person to apply the polymer and colorant powder thereto. The composition, which is also on the absorbent material, increases the weight of the absorbent material from 40% to 1000%. The invention also includes the article for applying makeup to one's person which is made by the above recited method.

18 Claims, No Drawings

METHOD OF APPLYING MAKEUP AND ARTICLE

FIELD OF THE INVENTION

The present invention relates to the field of makeup or cosmetic compositions which are carried as individual disposable devices to which a makeup formulation has been applied and dried and which delivers a smudge/smear resistant pigmented makeup composition to the face, head, body, hair, clothing or other surfaces of the user after being wetted, leaving a layer of color that dries to a smudge resistant, transfer resistant non-staining film which is soap and water washable.

BACKGROUND OF THE INVENTION

Cosmetic or makeup compositions which are designed to be applied to a wearer's body are usually comprised of a composition either pigmented or not, that is immediately usable or applicable to be applied to the body of the user. This presents somewhat of a problem in that the compositions must be provided in containers or otherwise so that they will not come into contact with other objects in a non-desired fashion as they are transported or carried on one's person. The need for containers creates additional expense in the form of the cost of the container and the cost of freight to ship the additional weight; the weight and space required for containers reduce the portability and convenience of the cosmetic composition in its ultimate and intended use.

An object of the present invention is to formulate a cosmetic composition and to provide an article of commerce and a method of use of the article so as to obviate these difficulties.

SUMMARY OF THE INVENTION

The present invention is directed to a composition, its absorption onto an absorbing medium such as natural or artificial sponges or other absorbent material which can be sold in commerce and when it is time to use the article of commerce, the absorbable material containing the composition is rewetted in water or a suitable volatile solvent which then in effect reactivates the composition which is then applied to the body of the user.

The composition as formulated, by weight is as follows: (a.) 20–98% volatile solvent, (b.) 0.1–20% polymer, and (c.) 0.1–40% powder.

It is also desirable although not absolutely essential that one add (d.) 0.01–5% gums or hydrophilic colloids and (e.) 0.01–5% surfactant (surface active agent).

The composition when suitably prepared is absorbed (soaked) into a natural or synthetic sponge or other absorbent material to totally impregnate the absorbent material which is thereafter dried either by natural or artificial heating means. Other absorbent materials are natural and synthetic fibers or the processed thread or cloth from them, such as cotton, wool, rayon, nylon and paper. The drying drives off the volatile solvent leaving the remaining materials in the absorbent material. The invention contemplates absorbing the cosmetic composition (after drying) on the absorbent material in amounts from 40% to 1000% based on the weight of the absorbent material. When it is desired to utilize the article of manufacture by the ultimate consumer, all one does is remoisten the absorbent material with water or another suitable volatile solvent. When the absorbent material is then applied to the skin or other parts of a person, the cosmetic composition comes off on the user and dries forming a smudge resistant film.

DETAILED DESCRIPTION

The term volatile solvent as utilized herein is a liquid material which is capable of dissolving and dispersing the other ingredients of the composition and then be evaporated either at ambient or higher temperatures. The dried composition is capable of being rewetted with water or another solvent, thereby reactivating the composition for later use. Volatile solvents that are utilizable in the present invention include water, alcohols (ie., ethanol, isopropanol, benzyl alcohol, butyl alcohol), hydrocarbons (ie., butane, isoparaffins, isopentane, mineral spirits, petroleum distillates, isododecane, deodorized kerosene, xylene), ketones (ie., acetone, MEK, MIBK), esters (ie., butyl acetate, ethyl acetate), silicones (ie., cyclomethicones, dimethicones) as well as others known to those skilled in the art.

The polymers that are usable in the present invention are synthetic and/or natural polymers which are selectively soluble in at least one of the solvents listed hereinabove. The families of these polymers/co-polymers are preferably vinyl derivatives, acrylic derivatives, and styrene derivatives. Some specific materials utilizable in and suitable for use in the present invention that meet this description are as follows:

Vinyl Derivatives
PVP/VA Copolymer, Butyl Ester of PVM/MA Copolymer, Ethyl Ester of PVM/MA Copolymer, Isopropyl Ester of PVM/MA Copolymer, Polyvinyl Alcohol, PVM/MA Copolymer, PVP, PVP/Eicosene Copolymer, PVP/Hexadecene Copolymer, PVP/NV Copolymer, PVP/Vinyl Acetate/Itaconic Acid Copolymer, Vinyl Acetate/Crotonic Acid Copolymer Acrylic Derivatives
Acrylamides, Acrylic/Acrylate Copolymers, All Carbomers, Ethylene/Acrylate Copolymer Acrylic-Vinyl Copolymers
PVP/Dimethylaminoethylmethacrylate Copolymer, PVP/Ethyl Methacrylate/Methacrylic Acid Copolymer, Sodium Acrylate/Vinyl Alcohol Copolymer Polymer Blend
Diethylene Glycolamine /Epichlorohydrin/Piperazine Copolymer Styrene
Styrene/Maleic Anhydride Copolymer, Sodium Polystyrene Sulfonate Some biological polymers (natural) and their derivatives are: colloidon, glyceryl starch, hyaluronic acid, sodium hyaluronate, glycogen, hydrogenated honey, mixed mucopolysaccharides, nitrocellulose, sodium chondroitin sulfate, wheat starch.

The powder or color component of the composition is generally a dry particulate material which may be either colored or non-colored (i.e. white). Suitable powders are as follows: D&C Red No. 7 Calcium Lake, D&C Red No. 30 Lake, D&C Red No. 40 Aluminum Lake, D&C Yellow No. 10 Aluminum Lake, Ext. D&C Yellow No. 7 Aluminum Lake, FD&C Blue No. 1 Aluminum Lake, FD&C Red No. 3 Aluminum Lake, FD&C Red. No. 4 Aluminum Lake, FD&C Yellow No. 5 Aluminum Lake, FD&C Yellow No. 6

Aluminum Lake, Aluminum Powder, Bismuth Oxychloride, Carmine, Chromium Hydroxide Green, Chromium Oxide Greens, Ferric Ammonium Ferrocyanide, Ferric Ferrocyanide, Guanine, Iron Oxides, Tin Oxide, Mica, Silver, Titanium Dioxide, Ultramarines, Zinc Oxide, and nacreous (pearlescent) powders.

As mentioned above it is usually desirable although not necessary to add gums or hydrophilic colloids to the composition and also surfactants.

The gums or hydrophilic colloids that are suitable for use in the composition of the present invention are Acacia, Algin, Carageenan, Cellulose Gum, Ethylcellulose, Guar Gum, Karaya Gum, Hydroxyethylcellulose, Carboxymethylcellulose, Hydroxyethyl Ethylcellulose, Hydroxypropylcellulose, Hydroxypropyl Guar, Hydroxypropyl Methylcellulose, Potassium Alginate, and Xanthan Gum.

Surfactants are surface active agents which exhibit the ability to lower the surface tension of water, or reduce the interfacial tension between two immiscible substances. General surfactant categories and a few samples are listed below:

1. Sulfosuccinates—Disodium Oleamido PEG-2 Sulfosuccinate, Dimethicone Copolyol Sulfosuccinate
2. Alkyl Sulfate—Sodium Lauryl Sulfate, TEA Lauryl Sulfate, Ammonium Lauryl Sulfate, Myristyl Sulfate
3. Alkyl Ether Sulfates—Sodium Laureth Sulfate, TEA Laureth Sulfate, Ammonium Laureth Sulfate
4. Sulfonic Acid—Sodium Methyl Cocoyl Taurate
5. Sarcosinates—Sodium Sarcosinate, Sodium Myristoyl Sarcosinate
6. Phosphorous Compounds—Sodium Laureth -4 Phosphate
7. Isethionates—Sodium Myristoyl Isethionate
8. Soaps—Sodium Laurate, Potassium Stearate, Sodium Cocoate
9. Sorbitan Derivatives—Polysorbate 20, Polysorbate 40, Polysorbate 60, Polysorbate 80, Polysorbate 61, Polysorbate 85
10. Amine Oxides—Cocamine Oxide, Oleamine Oxide
11. Alkoxylated Carboxylic Acids—PEG-150 Stearate
12. Alkoxylated Alcohols—Oleth-2, PEG-40 Castor Oil, Steareth-7
13. Alkanolamides—Cocamide DEA, Lauramide MEA, Soyamide DEA
14. Alkylamido Alkylamines—Disodium Cocoamphodiacetate
15. Alkyl Aryl Sulfonates—Sodium Xylenesulfonate
16. Silicones and Silanes—Dimethicone Copolyol
17. Ethers—PPG-Myristyl Ether
18. Amides—Sodium Lauroyl Glutamate, TEA-Lauroyl Glutamate It is also desirable, although not necessary that other ingredients be added to the composition in order to facilitate its manufacture and to facilitate its use. These materials will be indicated in the specific formulations that are given hereinafter and include chelating agents, anti-microbial agents, anti-foaming agents, fillers, desiccants, humectants, plasticizers and preservatives.

The invention of the present application will be hereinafter be described in connection with the following examples which are set forth for illustration.

EXAMPLE I

COLOR: RED

| PHASE | INGREDIENT | FUNCTION | % WT/WT |
|---|---|---|---|
| A. | DEIONIZED WATER | Diluent; volatile solvent | 81.01 |
|  | TETRASODIUM EDTA | Chelating agent; anti-microbial agent | 0.05 |
|  | SIMETHICONE | Anti-foaming agent | 0.01 |
|  | DISODIUM OLEAMIDO PEG-2 SULFOSUCCINATE | Surfactant, wetting agent | 0.03 |
| B. | TALC | Filler; desiccant | 3.00 |
|  | D&C RED No. 7 CALCIUM LAKE | Red pigment | 3.00 |
| C. | PROPYLENE GLYCOL | Humectant; plasticizer | 1.00 |
|  | XANTHAN GUM | Thickener; pigment suspension aid | 0.15 |
| D. | DEIONIZED WATER | Diluent; volatile solvent | 10.00 |
|  | PVP/VA COPOLYMER (COPOLYMER OF VINYL ACETATE and VINYL PYRROLIDONE MONOMERS) | Water-soluble polymer; resin; film former | 1.50 |
| E. | DMDM HYDANTOIN and 3-IODO-2PROPYNYLBUTYL CARBAMATE | Preservative; anti-microbial agent | 0.25 |
|  |  | TOTAL | 100.00 |

Procedure:
1. Add water of Phase A to primary vessel at room temperature.
2. Add ingredients of Phase A to water, and mix with moderate propeller agitation.
3. Add Phase B talc and pigments to Phase A and continue mixing with homomixer and propeller agitation for 30–45 minutes. Discontinue homomixer and allow batch to deairate.
4. Premix Phase C. With moderate propeller agitation, add Phase C to Phase AB. Clean out bottom valve and add back to batch. Mix for 1 hour with propeller agitation; make sure that the Xanthan Gum is completely Hydrated.
5. Premix Phase D and slowly add to Phase ABC. Mix for 20 minutes until PVP/VA W-735 resin has been well distributed throughout batch.
6. Add Phase E preservative and anti-microbial agent and mix for 20–30 minutes with slow to moderate propeller agitation until batch is uniform.

Observations: A sponge was immersed in this composition and then dried at 43 C for 24 hours. The dried sponge was rewetted, and used to apply the color to the skin. It transferred an opaque, red film to the skin that was transfer and rub resistant.

The following Example II is the same as Example I but identifying the materials by company or brand names.

EXAMPLE II

COLOR: RED

| PHASE | INGREDIENT | FUNCTION | % WT/WT |
|---|---|---|---|
| A | DEIONIZED WATER | Diluent; volatile solvent | 81.01 |
|  | TETRASODIUM EDTA | Chelating agent; anti-microbial | 0.05 |
|  | DOW CORNING ANTIFOAM A | Anti-foaming agent | 0.01 |
|  | STANDAPOL SH-135 | Surfactant; wetting agent | 0.03 |
| B | TALC - SUPRA A | Filler; dessicant | 3.00 |
|  | D&C RED No. 7 CALCIUM LAKE | Red pigment | 3.00 |
| C | PROPYLENE GLYCOL | Humectant; plasticizer | 1.00 |
|  | RHODIGEL 200 | Thickener; pigment suspending aid | 0.15 |
| D | DEIONIZED WATER | Diluent; volatile solvent | 10.00 |
|  | PVP/VA W-735 | water-soluble polymer; | 1.50 |
|  | (50% SOLUTION) | resin; film former |  |
| E | GLYDANT PLUS | Preservative; anti-microbial Agent | 0.25 |
|  |  | TOTAL | 100.00 |

The same mixing procedure was used as in Example I. Observations: A sponge was immersed in this composition and then dried at 43 C for 24 hours. The dried sponge was rewetted, and used to apply the color to the skin. It transferred an opaque, red film to the skin that was transfer and rub resistant.

EXAMPLES III, IV, V

COLORS: WHITE, BLACK, RED

|  |  | % WT/WT | | |
|---|---|---|---|---|
| PHASE | INGREDIENT | White 1189A | Black 1189B | Red 1189C |
| A. | DEIONIZED WATER | 63.39 | 63.39 | 84.39 |
|  | TETRASODIUM EDTA | 0.05 | 0.05 | 0.05 |
|  | DOW CORNING ANTIFOAM A | 0.02 | 0.02 | 0.02 |
|  | STANDAPOL SH-135 | 0.01 | 0.01 | 0.01 |
| B. | TALC - SUPRA A | 3.00 | 3.00 | 3.00 |
|  | 82140 BLACK IRON OXIDE | — | 24.00 | — |
|  | 09970 KOWET TiO2 | 24.00 | — | — |
|  | C6507 D&C RED #7 CALCIUM LAKE | — | — | 3.00 |
| C. | PROPYLENE GLYCOL | 1.00 | 1.00 | 1.00 |
|  | XANTHAN GUM - RHODIGEL 200 | 0.28 | 0.28 | 0.28 |
| D. | DEIONIZED WATER | 5.00 | 5.00 | 5.00 |
|  | PVP/VA W-735 (50% SOLUTION) | 3.00 | 3.00 | 3.00 |
| E. | GLYDANT PLUS | 0.25 | 0.25 | 0.25 |
|  | TOTAL | 100.00 | 100.00 | 100.00 |

The same mixing procedures were used as in Example I. Observations: Three sponges were immersed in these three compositions and then dried at 43 C for 24 hours. The dried sponges were re-wetted, and used to apply the colors to the skin. They transferred opaque, respectively, white, black and red films to the skin that were transfer and rub resistant.

EXAMPLE VI

COLOR: WHITE

| PHASE | INGREDIENT | % WT/WT |
|---|---|---|
| A. | DEIONIZED WATER | 67.39 |
|  | TETRASODIUM EDTA | 0.05 |
|  | DOW CORNING ANTIFOAM A | 0.02 |
|  | STANDAPOL SH-135 | 0.01 |
| B. | TALC - SUPRA A | 3.00 |
|  | KOWET TiO2 09970 | 20.00 |
| C. | PROPYLENE GLYCOL | 1.00 |
|  | XANTHAN GUM -RHODIGEL 200 | 0.28 |
| D. | DEIONIZED WATER | 5.00 |
|  | PVP/VA W-735 (50% SOLUTION) | 3.00 |
| E. | GLYDANT PLUS | 0.25 |
|  | TOTAL | 100.00 |

The same mixing procedure was followed as in Example I.

Observations: A sponge was immersed in this composition and then dried at 43 C for 24 hours. The dried sponge was re-wetted, and used to apply the color to the skin. It transferred an opaque, white film to the skin that was transfer and rub resistant.

Each of the above-referred to five compositions were incorporated into a synthetic sponge material having the following listed physical characteristics.

The sponge material is preferably a polyurethane foam or sponge-like material of similar properties (i.e., polystyrene foams or rubber compound foams), defined as an elastic porous mass of interfacing fibers, forming cells of various random and/or predetermined sizes and shapes, able when wetted to absorb water or various liquids of various viscosities. In compounding the sponge material, it could be more or less of fine or coarse cell, and should have the appropriate structure, density, resiliency, compressive strength, color, and chemical resistance properties. Naturally occurring sponges are also suitable as well as natural fibers such as wool and cotton as well as synthetic fibers such as rayon and nylon.

In each case the sponge material was completely immersed into the cosmetic composition until the sponge had absorbed all of the cosmetic composition that it was capable of absorbing. It was determined that the increase in weight of the sponge sample by absorbing the cosmetic composition increased the weight of the sponge by 40% to 1000%. In each instance the sponge material was allowed to dry naturally for a period of three days at which time most if not all of the volatile solvent material was driven off leaving the sponge in a dry condition.

To illustrate the increase in weight of the absorbent material with the cosmetic composition the composition of Example I was applied to completely saturate a polyurethane sponge originally weighing 0.033 grams. The sponge was dried and then was weighed giving total weight of about 0.048 grams or an increase of about 45%.

In another illustration the composition of Example XII was applied to the same weight and type of sponge. The resulting final weight of the product was about 0.283 grams giving an increase of about 860%.

The samples were then tested by reimmersing the sponge into water which caused the sponge to be wetted. Prior to rewetting the sponge would substantially not dispense color when it was rubbed against a person's skin. After rewetting, the sponge was applied to the face, head, body, hair, clothing and other surfaces of a user which left a color that dried to a smudge resistant, transfer resistant, non-staining film. The colored film was then easily washed off with soap and water.

Samples were also dried in a warm oven at 110° F. for a period of 16+ hours and the same results were obtained as described hereinabove.

In order to illustrate a composition in accord with the present invention without the gums or hydrophilic colloids and surfactants even though they are helpful, is illustrated in the following example identified as example VII.

EXAMPLE VII

| PHASE | INGREDIENT | % WT/WT |
|---|---|---|
| | COLOR: RED | |
| A | DEIONIZED WATER | 84.00 |
| B | C6501 D&C RED NO. 7 CALCIUM LAKE | 3.00 |
| C | DEIONIZED WATER | 10.00 |
| | PVP/VA-735 (50% SOLUTION) | 3.00 |
| | TOTAL | 100.00 |

Procedure: Same as prior formulas

Observations: A sponge was immersed in this composition and then dried at 43 C for 24 hours. The dried sponge was re-wetted, and used to apply the color to the skin. It transferred an opaque, red film to the skin that was transfer and rub resistant.

The composition of example VII was applied both to a natural sponge and a synthetic sponge in the manner illustrated hereinabove for examples 1–6 and the sponges were immersed in the composition until they had absorbed a maximum amount of the cosmetic composition. The amount of the composition absorbed for both the natural and synthetic sponges were on the order of that described hereinabove in examples 1–6. The sponges used in conjunction with example VII were oven dried for 16+ hours at 110° F. and when removed from the oven they were found to essentially not dispense color. When rewetted they applied a color to a person that was, upon drying, smudge resistant, transfer resistant, and a non-staining film. The film again was easily washed with soap and water.

The following examples illustrate variations in amount of ingredients in the formulas of the present invention. Examples VIII and IX show variations in the polymer loading, Examples X, XIII and XIV show variations in the amount and type of solvent, and Examples XI and XII show variations in the pigment loading.

EXAMPLE VIII

| PHASE | INGREDIENT | % WT/WT |
|---|---|---|
| | COLOR: RED | |
| A | DEIONIZED WATER | 42.39 |
| | TETRASODIUM EDTA | 0.05 |
| | DOW CORNING ANTIFOAM A | 0.02 |
| | STANDAPOL SH-135 | 0.01 |
| B. | C6507 D&C RED No. 7 CALCIUM LAKE | 3.00 |
| | TALC-SUPRA A | 3.00 |
| C. | PROPYLENE GLYCOL | 1.00 |
| | XANTHAN GUM - RHODIGEL 200 | 0.28 |
| D. | DEIONIZED WATER | 10.00 |
| | PVP/VA W-735 (50% SOLUTION) | 40.00 |
| E. | GLYDANT PLUS | 0.25 |
| | TOTAL | 100.00 |

Procedure: Same as prior formulas

Observations: A sponge was immersed in this composition and then dried at 43 C for 24 hours. The dried sponge was re-wetted, and used to apply the color to the skin. It transferred an opaque, red film to the skin that was transfer and rub resistant.

EXAMPLE IX

| PHASE | INGREDIENT | % WT/WT |
|---|---|---|
| | COLOR: RED | |
| A | DEIONIZED WATER | 87.29 |
| | TETRASODIUM EDTA | 0.05 |
| | DOW CORNING ANTIFOAM A | 0.02 |
| | STANDAPOL SH-135 | 0.01 |
| B. | C6507 D&C RED NO. 7 CALCIUM LAKE | 3.00 |
| | TALC - SUPRA A | 3.00 |
| C. | PROPYLENE GLYCOL | 1.00 |
| | XANTHAN GUM - RHODIGEL 200 | 0.28 |
| D. | DEIONIZED WATER | 5.00 |
| | PVP/VA W-735 (50% SOLUTION) | 0.10 |
| E. | GLYDANT PLUS | 0.25 |
| | TOTAL | 100.00 |

Procedure: Same as prior formulas

Observations: A sponge was immersed in this composition and then dried at 43 C for 24 hours. The dried sponge was re-wetted, and used to apply the color to the skin. It transferred an opaque, red film to the skin that was transfer and rub resistant.

EXAMPLE X

COLOR: BLACK

| PHASE | INGREDIENT | % WT/WT |
|---|---|---|
| A | DEIONIZED WATER | 20.00 |
|   | PVP/VA W-735 (50% SOLUTION) | 40.00 |
| B. | IRON OXIDE BLACK CG075 | 40.00 |
|   | TOTAL | 100.00 |

Procedure: Same as prior formulas
Observations: A sponge was immersed in this composition and then dried at 43 C for 24 hours. The dried sponge was re-wetted, and used to apply the color to the skin. It transferred an opaque, black film to the skin that was transfer and rub resistant.

EXAMPLE XI

COLOR: RED

| PHASE | INGREDIENT | % WT/WT |
|---|---|---|
| A | DEIONIZED WATER | 87.29 |
|   | TETRASODIUM EDTA | 0.05 |
|   | DOW CORNING ANTIFOAM A | 0.02 |
|   | STANDAPOL SH-135 | 0.01 |
| B. | TALC - SUPRA A | 3.00 |
|   | C6507 D&C RED NO. 7 CALCIUM LAKE | 0.10 |
| C. | PROPYLENE GLYCOL | 1.00 |
|   | XANTHAN GUM - RHODIGEL 200 | 0.28 |
| D. | DEIONIZED WATER | 5.00 |
|   | PVP/VA W-735 (50% SOLUTION) | 3.00 |
| E. | GLYDANT PLUS | 0.25 |
|   | TOTAL | 100.00 |

Procedure: Same as prior formulas
Observations: A sponge was immersed in this composition and then dried at 43 C for 24 hours. The dried sponge was re-wetted, and used to apply the color to the skin. It transferred a transparent, light pink film to the skin that was transfer and rub resistant.

EXAMPLE XII

COLOR: BLACK

| PHASE | INGREDIENT | % WT/WT |
|---|---|---|
| A | DEIONIZED WATER | 55.62 |
|   | TETRASODIUM EDTA | 0.05 |
|   | DOW CORNING ANTIFOAM A | 0.02 |
|   | STANDAPOL SH-135 | 0.01 |
| B. | IRON OXIDE BLACK CG 075 | 40.00 |
| C. | PROPYLENE GLYCOL | 1.00 |
|   | XANTHAN GUM - RHODIGEL 200 | 0.05 |
| D. | GLYDANT PLUS | 0.25 |
|   | TOTAL | 100.00 |

Procedure: Same as prior formulas
Observations: A sponge was immersed in this composition and then dried at 43 C for 24 hours. The dried sponge was re-wetted, and used to apply the color to the skin. It transferred an opaque, black film to the skin that was transfer and rub resistant.

EXAMPLES XIII and XIV

COLOR: WHITE

|   |   | % WT/WT | |
|---|---|---|---|
| PHASE | INGREDIENT | XIV | XIII |
| A | DEIONIZED WATER | — | 42.43 |
|   | SD ALCOHOL 40-2 | 52.60 | 20.00 |
|   | TETRASODIUM EDTA | — | 0.01 |
|   | DOW CORNING ANTIFOAM A | — | 0.02 |
|   | STANDAPOL SH-135 | — | 0.01 |
| B. | 09970 KOWET TITANIUM DIOXIDE | 20.00 | 20.00 |
|   | TALC - SUPRA A |   | 3.00 |
| C. | PROPYLENE GLYCOL | 1.00 | 1.00 |
|   | XANTHAN GUM - RHODIGEL 200 | — | 0.28 |
|   | SD ALCOHOL 40-2 | 20.00 | 5.00 |
|   | KLUCEL HFF-99 | 0.40 | — |
| D. | DEIONIZED WATER | — | 5.00 |
|   | PVP/VA W-735 (50% SOLUTION) | 3.00 | 3.00 |
| E. | GLYDANT PLUS | — | 0.25 |
|   | TOTAL | 100.00 | 100.00 |

Procedure: Same as prior formulas
Observations: Sponges were immersed in this composition and then dried at 43 C for 24 hours. The dried sponges were re-wetted, and used to apply the color to the skin. It transferred an opaque, white film to the skin that was transfer and rub resistant.

It will be understood by those skilled in the art that the absorbent material, i.e. the natural or synthetic sponge or fiber as described above is best used by attaching it by glue or any other suitable mechanism to a plastic, metal or a wooden handle. This facilitates handling of the article of manufacture that has been described herein and enables the person to easily utilize the article.

The following formula illustrates the use of nacreous powder (gold pearl) in a composition under the present invention.

EXAMPLE XV

COLOR: GOLD PEARL

| PHASE | INGREDIENT | % WT/WT |
|---|---|---|
| A | DEIONIZED WATER | 75.39 |
|   | TETRASODIUM EDTA | .05 |
|   | DOW CORNING ANTIFOAM A | 0.02 |
|   | STANDAPOL SH-135 | 0.01 |
| B. | TALC - SUPRA A | 3.00 |
|   | 35060 YELLOW IRON OXIDE | 2.00 |
| C. | PROPYLENE GLYCOL | 1.00 |
|   | XANTHAN GUM - RHODIGEL 200 | 0.28 |
| D. | DEIONIZED WATER | 5.00 |
|   | PVP/VA W-735 (50% SOLUTION) | 3.00 |
| E. | GLYDANT PLUS | 0.25 |
|   | TIMIRON MP-25 GOLD PLUS #017221 | 6.00 |
|   | TOTAL | 100.00 |

Procedure:
1. Add water of Phase A to primary vessel at RT.
2. Add ingredients of Phase A to water, and mix with moderate propeller agitation.
3. Add Phase B talc and pigments to Phase A and continue mixing with homomixer and propeller agitation for 30–45 minutes. Discontinue homomixer and allow batch to deairate.

4. Premix Phase C. With moderate propeller agitation, add Phase C to Phase AB. Clean out bottom valve and add back to batch. Mix for 1 hour with propeller agitation; make sure that the Xanthan Gum is completely hydrated.
5. Premix Phase D and slowly add to Phase ABC. Mix for 20 minutes and PVP/VA W-735 resin has been well distributed throughout batch.
6. Add Phase E Glydant preservative and Gold Powder Pearl and mix for 20–30 minutes with slow to moderate propeller agitation and sweep until batch is uniformed and Pearl has been well distributed throughout batch.

Observations: Sponges were immersed in this composition and then dried at 43 C for 24 hours. The dried sponges were re-wetted, and used to apply the color to the skin. It transferred an opaque, gold film to the skin that was transfer and rub resistant.

The following example XVI shows the use of polyvinylpyrrolidone (PVP) as the polymer in the composition.

-continued

COLOR: RED

| PHASE | INGREDIENT | % WT/WT |
|---|---|---|
| | XANTHAN GUM - RHODIGEL 200 | 0.28 |
| D. | DEIONIZED WATER | 5.00 |
| | PVP K-90 (100%) | 1.50 |
| D. | GLYDANT PLUS | 0.25 |
| | TOTAL | 100.00 |

Procedure: Same as prior formulas

Observations: Sponges were immersed in this composition and then dried at 43 C for 24 hours. The dried sponges were re-wetted, and used to apply the color to the skin. It transferred an opaque, red film to the skin that was transfer and rub resistant.

The following is a chart showing the % uptakes by the absorbent material of wet and dry material in the composition. This chart relates to specific compositions disclosed herein and other lab examples.

Sponge Uptake Evaluation (3 samples each formula)

| Sample Number | Formula Number of Color Concentrate (Example #) | Applicator Tare Wt. (g) (with handle) | Gross Weight (g) (Wet-with Handle) | Net Weight (g) (wet conc.) | % Weight Increase (wet) | Gross Weight (g) Dry (with handle) | Net Weight (g) of Dry Color conc. | % Weight Increase Dry Color Concentrate |
|---|---|---|---|---|---|---|---|---|
| 1 | CS 0003 (XI) | 0.78 | 1.32 | 0.54 | 1636 | 0.80 | 0.02 | 60.61 |
| 2 | CS 0003 | 0.74 | 1.25 | 0.51 | 1546 | 0.76 | 0.02 | 60.61 |
| 3 | CS 0003 | 0.76 | 1.29 | 0.53 | 1606 | 0.78 | 0.02 | 60.61 |
| 4 | CH-1189A(III) | 0.73 | 1.45 | 0.72 | 2182 | 0.94 | 0.21 | 636.36 |
| 5 | CH-1189A | 0.74 | 1.41 | 0.67 | 2030 | 0.93 | 0.19 | 575.76 |
| 6 | CH-1189A | 0.74 | 1.50 | 0.76 | 2303 | 0.96 | 0.22 | 666.67 |
| 7 | CS 0004 (XII) | 0.78 | 1.40 | 0.62 | 1879 | 1.02 | 0.24 | 727.27 |
| 8 | CS 0004 | 0.77 | 1.52 | 0.75 | 2273 | 1.07 | 0.30 | 909.09 |
| 9 | CS 0004 | 0.71 | 1.40 | 0.69 | 2091 | 0.99 | 0.28 | 848.48 |
| 10 | CH-1146 (VI) | 0.78 | 1.49 | 0.71 | 2152 | 0.95 | 0.17 | 515.15 |
| 11 | CH-1146 | 0.74 | 1.36 | 0.62 | 1879 | 0.88 | 0.14 | 424.24 |
| 12 | CH-1146 | 0.75 | 1.45 | 0.70 | 2121 | 0.92 | 0.17 | 515.15 |
| 13 | CS 0005 (IX) | 0.74 | 1.20 | 0.46 | 1394 | 0.77 | 0.03 | 90.91 |
| 14 | CS 0005 | 0.79 | 1.22 | 0.43 | 1303 | 0.82 | 0.03 | 90.91 |
| 15 | CS 0005 | 0.71 | 1.18 | 0.47 | 1424 | 0.75 | 0.04 | 121.21 |
| 16 | CS 0013 (VIII) | 0.76 | 1.41 | 0.65 | 1970 | 0.95 | 0.19 | 575.76 |
| 17 | CS 0013 | 0.70 | 1.30 | 0.60 | 1818 | 0.88 | 0.18 | 545.45 |
| 18 | CS 0013 | 0.72 | 1.31 | 0.59 | 1788 | 0.88 | 0.16 | 484.85 |
| 19 | CS 0011 (XV) | 0.83 | 1.41 | 0.58 | 1758 | 0.93 | 0.10 | 303.03 |
| 20 | CS 0011 | 0.71 | 1.32 | 0.61 | 1885 | 0.81 | 0.10 | 303.03 |
| 21 | CS 0011 | 0.74 | 1.36 | 0.62 | 1879 | 0.85 | 0.11 | 333.33 |
| 22 | CS 0012 | 0.82 | 1.44 | 0.62 | 1879 | 0.95 | 0.13 | 393.94 |
| 23 | CS 0012 | 0.78 | 1.39 | 0.61 | 1849 | 0.90 | 0.12 | 363.64 |
| 24 | CS 0012 | 0.78 | 1.36 | 0.58 | 1758 | 0.89 | 0.11 | 333.33 |
| 25 | CS 0016 (XVI) | 0.70 | 1.20 | 0.50 | 1515 | 0.75 | 0.05 | 151.52 |
| 26 | CS 0016 | 0.75 | 1.25 | 0.50 | 1515 | 0.79 | 0.04 | 121.21 |
| 27 | CS 0016 | 0.74 | 1.23 | 0.49 | 1485 | 0.77 | 0.03 | 90.91 |

EXAMPLE XVI

COLOR: RED

| PHASE | INGREDIENT | % WT/WT |
|---|---|---|
| A | DEIONIZED WATER | 85.89 |
| | TETRASODIUM EDTA | .05 |
| | DOW CORNING ANTIFOAM A | 0.02 |
| | STANDAPOL SH-135 | 0.01 |
| B. | TALC-SUPRA A | 3.00 |
| | C6507 D & C RED NO. 7 CALCIUM LAKE | 3.00 |
| C. | PROPYLENE GLYCOL | 1.00 |

The potential applications for the article and the method of using the article can be found in several industries including, the Halloween industry, the cosmetic personal-care industry i.e. as eye shadow, rouge or blusher, alopecia cover cream, blemish cover, with or without medication, under eye cover, nail color, hair color, face makeup, theatricalmakeup, leg makeup, varicose vein coverup, sports under eye black, sunscreen nose coat, mortuary makeup, camouflage makeup, lipstick and the like; as well as in the toy industry, i.e. as makeup for children, fantasy makeup, nail color, hair color, and the like.

It will thus be seen from a review of the above that there has been disclosed herein an article of commerce and a method of use of the same which provides a dry cosmetic composition on an absorbent material which essentially will not dispense thecolor contained therein until it is rewetted in water or a suitable volatile solvent. Once rewetted the color may be applied to one's person and ends up as a smudge resistant, transfer resistant, non-staining film which can be easily washed off with soap and water when the person using the cosmetic desires.

The invention has been described in detail with particular emphasis on the preferred embodiments thereof, but it should be understood that variations and modifications within the spirit and scope of the invention may occur to those skilled in the art to which the invention pertains.

What is claimed is:

1. A method of applying makeup to one's person including the steps of preparing a liquid makeup composition by mixing together a volatile solvent, a soluble polymer and a colorant powder, said soluble polymer being resoluble, absorbing said liquid composition into and on an absorbent material, drying said composition into and on said absorbent material to remove said volatile solvent, subjecting said absorbent material with said dried composition therein and thereon to a volatile solvent to wet said composition, and rubbing said wetted absorbent material with said composition therein and thereon to one's person to apply said polymer and colorant powder thereto, redrying said wetted absorbent material with said composition therein and thereon wherein it can again be subjected to a volatile solvent and again rubbed on one's person to again apply said polymer and colorant powder thereto.

2. The method of claim 1 wherein said absorbent material is selected from the group consisting of natural sponge, synthetic sponge and fiber.

3. The method of claim 2 wherein said volatile solvent is present in an amount in the range of 20–98%;

the polymer in the range of 0.1–20%; and the colorant powder in the range of 0.1–40%;

all by weight percent based on the total weight of the liquid makeup composition.

4. The method of claim 3 wherein said volatile solvent is selected from the group consisting of water, alcohols, hydrocarbons, ketones, esters, silicones, and blends thereof.

5. The method of claim 4 wherein said polymer is selected from the group consisting of biological polymers, vinyl derivatives, acrylic derivatives, styrene derivatives and mixtures thereof.

6. The method of claim 5 wherein said colorant powder is selected from the group consisting of D&C Red No. 7 Calcium Lake, D&C Red No. 30 Lake, D&C Red No. 40 Aluminum Lake, D&C Yellow No. 10 Aluminum Lake Ext. D&C Yellow No. 7 Aluminum Lake, FD&C Blue No. 1 Aluminum Lake, FD&C Red No. 3 Aluminum Lake, FD&C Red. No. 4 Aluminum Lake, FD&C Yellow No. 5 Aluminum Lake, FD&C Yellow No. 6 Aluminum Lake, Aluminum Powder Bismuth Oxychloride, Carmine, Chromium Hydroxide Green, Chromium Oxide Greens, Ferric Ammonium Ferrocyanide, Ferric Ferrocyanide, Guanine, Iron Oxides, Tin Oxide, Mica, Silver, Titanium Dioxide, Ultramarines, and nacreous (pearlescent) pigments.

7. The method of claim 6 wherein gums and/or hydrophilic colloids are added to said composition in the amount of 0.01–5% by weight based on the total weight of said composition.

8. The method of claim 5 wherein said gums and/or hydrophilic colloids are selected from the group consisting of Acacia, Algin, Cellulose Gum, Ethylcellulose, Guar Gum, Hydroxyethylcellulose, Carboxymethylcellulose, Hydroxyethyl Ethylcellulose, Hydroxypropylcellulose, Hydroxypropyl Guar, Hydroxypropyl Methylcellulose, Potassium Alginate, and Xanthan Gum.

9. The method of claim 8 wherein a surfactant is added to said composition in the amount of 0.01–5% by weight based on the total weight of said composition.

10. The method of claim 9 wherein said surfactant is selected from the group consisting of Sulfosuccinates, Alkyl Sulfates, Alkyl Ether Sulfates, Sulfonic Acid, Sarcosinates, Phosphorous Compounds, Isethionates, Soaps, Sorbitan Derivatives, Amine Oxides, Alkoxylated Carboxylic Acids, Alkoxylated Alcohols, Alkanolamides, Alkylamido Alkylamines, Alkyl Aryl Sulfonates, Silicones and Silanes, Ethers, and Amides.

11. The method of claim 1 wherein the weight of said absorbent material is increased by 40% to 1000% after drying.

12. An article for applying makeup to one's person including an absorbent member in which has been absorbed a cosmetic composition comprising a volatile solvent, a soluble polymer and a colorant powder, said volatile solvent having been evaporated therefrom, said soluble polymer being resoluble, and wherein said cosmetic composition absorbed in said absorbent member from which solvent has been evaporated is capable of being wetted in a volatile solvent such that said soluble polymer is resoluble and wherein said wetted composition absorbed in said absorbent member may be applied by engaging said absorbent member with one's person, said absorbent member being capable of being redryed and rewetted a plurality of times to apply said rewetted composition to one's person a plurality of times.

13. The article of claim 12 wherein said absorbent material is selected from the group consisting of natural sponge, synthetic sponge and absorbent fiber.

14. The article of claim 13 wherein the cosmetic composition absorbed on said absorbent material increases the weight of the article by 40% to 1000%.

15. The article of claim 13 wherein said volatile solvent is present in an amount in the range of 20–98%;

the polymer in the range of 0.1–20%; and the colorant powder in the range of 0.1–40%;

all by weight percent based on the total weight of the liquid makeup composition.

16. The article of claim 15 wherein said volatile solvent is selected from the group consisting of water, alcohols hydrocarbons, ketones, esters, silicones, and blends thereof.

17. The article of claim 16 wherein said polymer is selected from the group consisting of biological polymers, vinyl derivatives, acrylic derivatives, styrene derivatives and mixtures thereof.

18. The article of claim 17 wherein said colorant powder is selected from the group consisting of D&C Red No. 7 Calcium Lake, D&C Red No. 30 Lake, D&C Red No. 40 Aluminum Lake, D&C Yellow No. 10 Aluminum Lake, Ext. D&C Yellow No. 7 Aluminum Lake, FD&C Blue No. 1 Aluminum Lake, FD&C Red No. 3 Aluminum Lake, FD&C Red No. 4 Aluminum Lake, FD&C Yellow No. 5 Aluminum Lake, FD&C Yellow No. 6 Aluminum Lake, Aluminum Powder, Bismuth Oxychloride, Carmine, Chromium Hydroxide Green, Chromium Oxide Greens, Ferric Ammonium Ferrocyanide, Ferric Ferrocyanide, Guanine, Iron Oxides, Tin Oxide, Mica, Silver, Titanium Dioxide, Ultramarines, Zinc Oxide, and nacreous (pearlescent) powders.

* * * * *